(12) United States Patent
Rolnick et al.

(10) Patent No.: US 7,004,918 B2
(45) Date of Patent: Feb. 28, 2006

(54) LOW COST ORTHOSIS FOR TOE INJURIES

(76) Inventors: Michael Alan Rolnick, 12533 Folly Quarter Rd., Ellicott City, MD (US) 21042; Mathew Ferry Warden, 12 Littell St., Brookline, MA (US) 02446; Robert Allen Van Wyk, 10801 Starkey Rd #104-16, Largo, FL (US) 33777

( * ) Notice: Subject to any disclaimer, the term of this patent is extended or adjusted under 35 U.S.C. 154(b) by 303 days.

(21) Appl. No.: 10/442,195

(22) Filed: May 20, 2003

(65) Prior Publication Data

US 2004/0068216 A1 Apr. 8, 2004

Related U.S. Application Data

(60) Provisional application No. 60/382,240, filed on May 23, 2002.

(51) Int. Cl.
A61F 5/00 (2006.01)

(52) U.S. Cl. .......................................... 602/30; 602/23
(58) Field of Classification Search ................... 602/30, 602/23, 22, 60, 61, 62; 128/877, 878, 879, 128/882
See application file for complete search history.

(56) References Cited

U.S. PATENT DOCUMENTS

| | | | | |
|---|---|---|---|---|
| 2,725,648 A | * | 12/1955 | Kirk et al. | 602/23 |
| 4,446,856 A | * | 5/1984 | Jordan | 602/27 |
| 4,602,626 A | * | 7/1986 | Johnson et al. | 602/27 |
| 4,677,767 A | * | 7/1987 | Darby | 36/102 |
| 4,821,431 A | * | 4/1989 | Rieffel | 36/88 |
| 4,914,837 A | * | 4/1990 | Rieffel | 36/88 |
| 5,078,128 A | * | 1/1992 | Grim et al. | 602/23 |
| 5,138,777 A | * | 8/1992 | Darby | 36/88 |
| 5,425,701 A | * | 6/1995 | Oster et al. | 602/23 |
| 5,569,174 A | * | 10/1996 | Varn | 602/27 |
| 5,577,998 A | * | 11/1996 | Johnson et al. | 602/5 |
| 5,592,757 A | * | 1/1997 | Jackinsky | 36/114 |
| 5,665,059 A | * | 9/1997 | Klearman et al. | 602/27 |
| 5,799,659 A | * | 9/1998 | Stano | 128/882 |
| 5,827,210 A | * | 10/1998 | Antar et al. | 602/23 |
| 5,833,639 A | * | 11/1998 | Nunes et al. | 602/23 |
| 5,853,380 A | * | 12/1998 | Miller | 602/27 |
| 5,887,591 A | * | 3/1999 | Powell et al. | 128/882 |
| 5,940,992 A | * | 8/1999 | Darby | 36/110 |
| 6,017,042 A | * | 1/2000 | Paris | 280/14.21 |
| 6,282,818 B1 | * | 9/2001 | Lu | 36/110 |
| 6,302,858 B1 | * | 10/2001 | DeToro et al. | 602/5 |
| 6,361,515 B1 | * | 3/2002 | Gilmour | 602/27 |
| 6,423,021 B1 | * | 7/2002 | Gallegos | 602/23 |

(Continued)

*Primary Examiner*—Henry Bennett
*Assistant Examiner*—Shumaya B. Ali
(74) *Attorney, Agent, or Firm*—Chalin A. Smith; Smith Patent Consulting

(57) ABSTRACT

A low-cost orthosis for the treatment of toe injuries is disclosed. The orthosis is a bilateral, monolithic structure molded from polymeric foam material and having an upper portion adapted to surround the heel, dorsal portions, and toes of a foot, and a lower portion forming an outsole. The outsole has a wedge-shaped, proximal portion which elevates the forefoot, the proximal portion terminating in a cylindrical radius positioned beneath the ball of a user's foot. The distal portion of the outsole is recessed so that during use the orthosis can pivot on the fulcrum formed by the previously described radius, as would occur during ambulation, without the distal end of the orthosis contacting the floor. An insole, formed by the upper surfaces of the outsole of the orthosis is generally planar with a distally positioned recess in the area of a user's toes. The orthosis disclosed mimics true physiology so as to allow a heel strike, pivoting on the ball of the foot, and launching from the ball of the foot while preventing weight-bearing flexion and extension of the toes and protecting the toes from further injury.

48 Claims, 6 Drawing Sheets

U.S. PATENT DOCUMENTS

| | | | | |
|---|---|---|---|---|
| 6,428,493 B1 | * | 8/2002 | Pior et al. | 602/10 |
| 6,432,073 B1 | * | 8/2002 | Pior et al. | 602/10 |
| 6,478,762 B1 | * | 11/2002 | Varn | 602/27 |
| 6,517,505 B1 | * | 2/2003 | Veldman | 602/27 |
| 6,581,304 B1 | * | 6/2003 | Mitchell | 36/77 R |
| 6,647,986 B1 | * | 11/2003 | Korotko et al. | 128/877 |
| 6,655,051 B1 | * | 12/2003 | Peche et al. | 36/103 |
| 6,701,643 B1 | * | 3/2004 | Geer et al. | 36/97 |
| 6,785,984 B1 | * | 9/2004 | Jackinsky | 36/28 |
| 2003/0033732 A1 | * | 2/2003 | Jackinsky | 36/28 |
| 2003/0051372 A1 | * | 3/2003 | Lyden | 36/27 |
| 2004/0082895 A1 | * | 4/2004 | Price et al. | 602/28 |

* cited by examiner

SECTION A-A

LOW COST ORTHOSIS FOR TOE INJURIES

This application claims the benefit of provisional application 60/382,240 filed May 23, 2002.

BACKGROUND OF THE INVENTION

This invention relates to the treatment of injuries to the foot, and more particularly, to a low cost orthosis for treating patients with toe injuries.

Toe injuries are extremely common, both sprains and fractures. Treatment generally consists of reducing any fracture and splinting the toe by taping it to an adjacent uninjured toe with gauze between the toes. The patient is given additional padding and tape so that he can revise the splinting which will be required for about one week. Additional treatment includes rest, ice, elevation and anti-inflammatory medication. Comfort may be provided by use of a cane, crutches, or other method which minimizes weight-bearing flexion and extension of the toes. Wearing shoes generally causes increased pain due to confinement and rubbing of the toe by the shoe. Some patients find that wearing a soft slipper or a sneaker with the toe section cut off gives comfort. Symptoms generally improve within one week.

The treatment for toes following surgical correction of mallet toe, hammer toe, or claw toe, or following the removal of hard or soft corns also requires that weight-bearing flexion and extension of the affected toe be prevented and that the toe be protected from further injury due to contact with fixed objects. The treatment of inflammations and infections of the toes is similar. Patient comfort is enhanced by preventing weight-bearing movement of the toes and preventing their contact with other objects.

Common to all treatments is that movement of the injured toe be prevented. This severely limits patient mobility since walking involves a heel strike, pivoting on the ball of the foot, and launching, with the ball of the foot and the toes supporting the patient's weight during the launch. Weight-bearing flexion and extension of the toes occurs with each step. Use of crutches can limit this flexion and extension, however, patient mobility is limited and no protection is given to the injured toe to prevent additional injury due to accidental contact with fixed objects. Wearing a soft slipper or a sneaker with the toe section cut off, while providing some patient comfort, will often not totally eliminate weight-bearing flexion and extension of the toes and will expose the injured toes to additional injury since the toes are unprotected.

Orthoses exist for the treatment of other injuries to the forefoot. Typical of these is the Orthowedge Healing Shoe (Markell Shoe Company, Yonkers, N.Y.) which, according to their literature, "elevates and unweights the forefoot after surgery or injury". The outsole of the shoe is much thicker than that of a standard shoe so as to form a platform, and is angled somewhat so that the forefoot is elevated above the heel area. The weight-bearing portion of the outsole extends from the heel of the shoe a distance which places its distal end under the distal half of the arch. The outsole then tapers abruptly to a reduced thickness which extends distally a distance which places the distal end of the outsole slightly beyond the distal end of the wearer's toes. The toe region of the shoe is open so as to minimize contact with the injured region of the foot. The upper portion of the shoe is made from soft, compliant materials and has a dorsal split along its top surface. This allows the foot to be inserted into the shoe with a motion that is substantially orthogonal to the sole of the shoe thereby preventing inadvertent contact between the injured forefoot and the shoe. This is in contrast to a standard shoe which requires insertion of the forefoot with a motion substantially parallel to the insole of the shoe. The Markell shoe elevates the forefoot so as to prevent the distal end of the orthosis from contacting the floor during walking. Pivoting and launch occur from the distal end of the weight-bearing portion of the outsole, which is beneath the metatarsal arch of the user's foot. This unnatural pivot and launch, and the thickness of the platform in the heel area make walking ungainly. The unnatural pivoting effect is amplified by the distal limit of the weight-bearing region which is a defined edge rather than a radius. Because the insole is essentially a flat surface, during pivot and launch some weight-bearing flexion of the toes still occurs. Additionally, an orthosis of this type is of rather complex construction, containing a variety of materials and designed to have a life significantly longer than that generally required for treating a toe injury.

No effective orthosis is available for the treatment of injuries, infections, or inflammation of the toes.

It is accordingly an object of this invention to provide an orthosis for treatment of toe injuries.

It is also an object of this invention to provide an orthosis for toe injuries which mimics true physiology during walking so as to minimize its effect on the patient's gait.

It is also an object of this invention to provide an orthosis for toe injuries which allows a launch from the ball of the foot without load-bearing flexion or extension of the toes.

It is also an object of this invention to provide an orthosis for toe injuries which protects the toes from further injury.

It is also an object of this invention to provide an orthosis for toe injuries which is lightweight and effective.

It is further an object of this invention to provide an orthosis for toe injuries which is of simple construction.

It is finally an object of this invention to provide an orthosis for treatment of toe injuries which is low cost.

It is further an object of this invention to provide an orthosis for toe injuries which can be used on either the left or the right foot.

SUMMARY OF THE INVENTION

These and other objects are accomplished by the invention herein disclosed consisting of a generally shoe-shaped orthosis molded as a monolithic structure from a semi-rigid polymeric foam material such as closed cell polypropylene foam. The insole of the orthosis has a planar, proximal, weight-bearing portion extending from the heel to the distal end of the metatarsals of a user's foot, and a planar, distal portion, generally parallel to the aforementioned proximal portion but recessed a distance below this proximal portion. The proximal portion increases in width distally from the heel to the distal limit of the portion so as to generally conform to the shape of a user's foot. The distal portion is of a constant width equal to the width of the distal end of the proximal portion of the insole.

The outsole of the orthosis has a proximal, weight-bearing region and a distal region. The proximal end of the proximal region has a thickness approximating that of the heel of a standard shoe. The proximal region increases in thickness along its distat length, the region ending slightly distal to the distal end of the metatarsals of a user's foot. The distal end of the weight-bearing region forms a lateral axially, cylindrical radius extending the width of the outsole. The non-weight-bearing, distal portion of the outsole is of reduced thickness, is displaced vertically above the distal end of the weight-bearing region and is angled upward so that the orthosis can pivot on the previously described cylindrical radius at the distal end of the proximal portion, through an angle as would occur during walking, without the distal end of the outsole contacting the floor.

The previously described insole is inclined upward by the increasing thickness of the weight-bearing portion of the outsole. The proximal, heel portion of the insole is surrounded by a more or less vertical wall extending to a height slightly below a user's ankle, the wall being of sufficient thickness, rigidity and height to prevent the heel from lifting from the interior weight-bearing surface when the orthosis is pivoted on the fulcrum formed by the cylindrical radius at the distal end of the proximal portion of the outsole. Two pliable, longitudinal, laterally opposed walls surround the approximately distal half of the proximal portion of the insole and the recessed distal portion of the insole. These longitudinal walls have a height such that, when wrapped partially over both sides of the dorsum of a user's foot, a small gap remains between the ends of these walls atop the dorsum of the foot. The far distal portions of the longitudinal walls wrap over a more or less vertical, lateral wall at the distal end of the distal region of the insole so as to form a toe box of sufficient height and width to protect the toes of a user's foot. The distal end, lateral wall is of sufficient thickness to protect a user's toes from injury due to contact between the orthosis and a fixed object during ambulation. A securing means such as hook and loop straps secures the longitudinal walls about the foot.

During use, a user's toes are surrounded by a toe box formed on the bottom by the recessed distal region of the insole, with lateral sides and top formed by the distal portion of the wrapped longitudinal walls and on its distal end by the wall at the distal end of the recessed distal region. This toe box is of sufficient size to preclude contact between the injured toe with its associated dressing and the interior of the orthosis. During ambulation, the orthosis pivots on the fulcrum formed by the distal radius of the weight-bearing portion of the outsole so as to give maximum launch. However, the distal, non-weight bearing portion of the outsole does not contact the floor. Since the heel of the orthosis is comparable in height to that of a standard shoe, walking with a somewhat normal gait is possible if a shoe having a comparable heel thickness is worn on the uninjured foot. The device is designed in such a manner that it can be molded complete in a monolithic manner to its final shape in a single operation thereby allowing it to be produced at low cost. Because the orthosis is molded from polypropylene or similar foam, it has sufficient use life to treat most toe injuries and is lightweight. The bilateral symmetry of the device allows it to be used on either the left or right foot. The orthosis is molded in a range of incremental sizes. A cloth liner conforming generally to the interior shape of the orthosis, and having a dorsal split may be added to improve user comfort.

The more important features of the invention have been outlined rather broadly in order that the detailed description thereof that follows may be better understood, and in order that the present contribution to the art may be better appreciated. There are, of course, additional features of the invention that will be descried hereinafter and which will form the subject matter of the claims appended hereto.

DESCRIPTION OF THE PREFERRED EMBODIMENT

Figure 1:
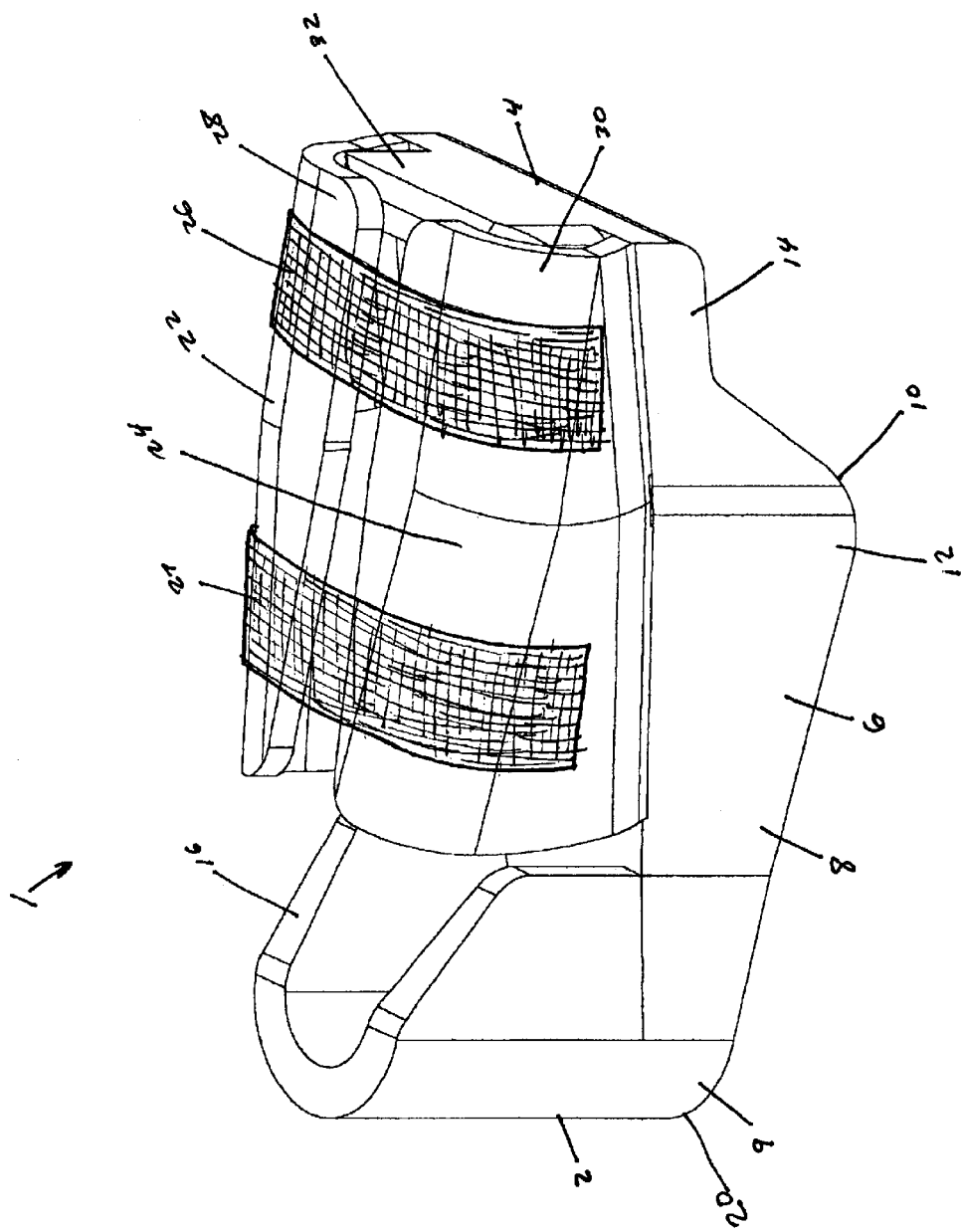
FIG. 1 is a perspective view of an orthosis formed in accordance with the principles of this invention.
Figure 2:
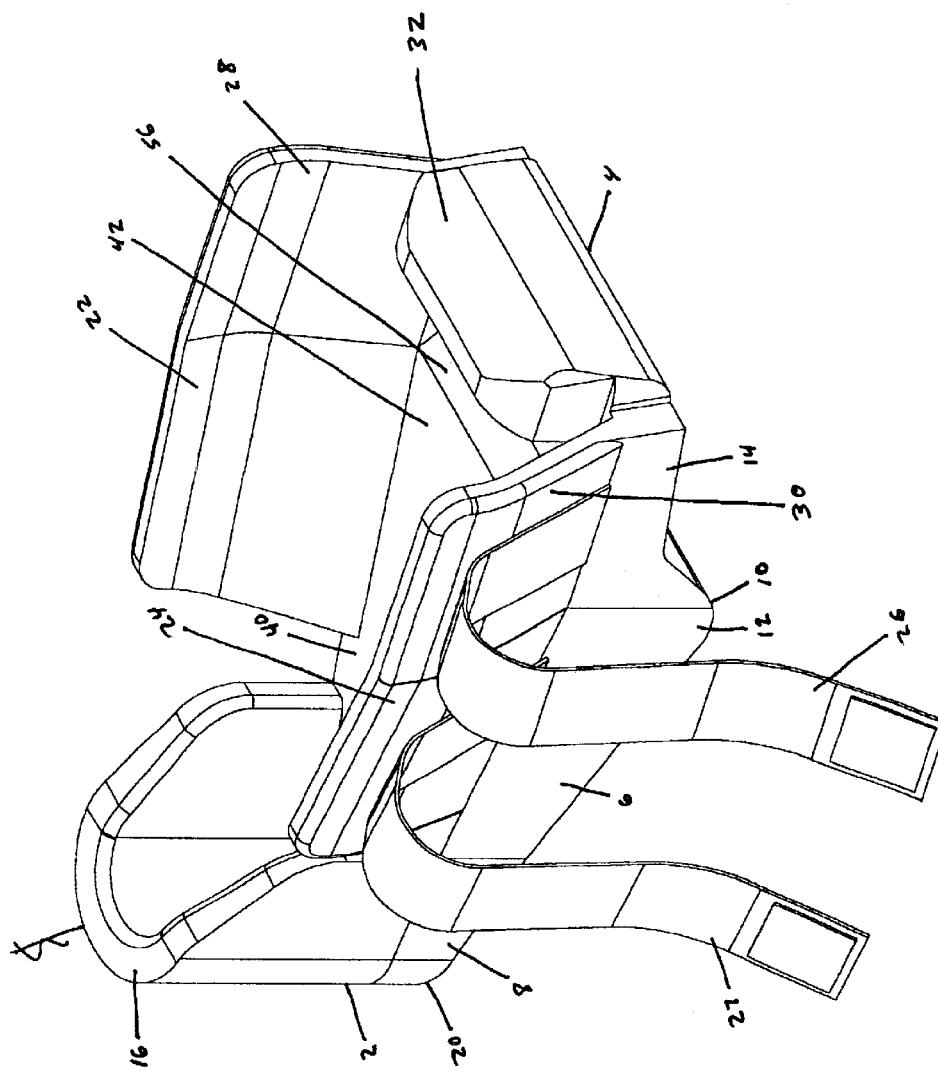
FIG. 2 is a perspective view of an orthosis formed in accordance with the principles of this invention as it appears prior to use.
Figure 3:
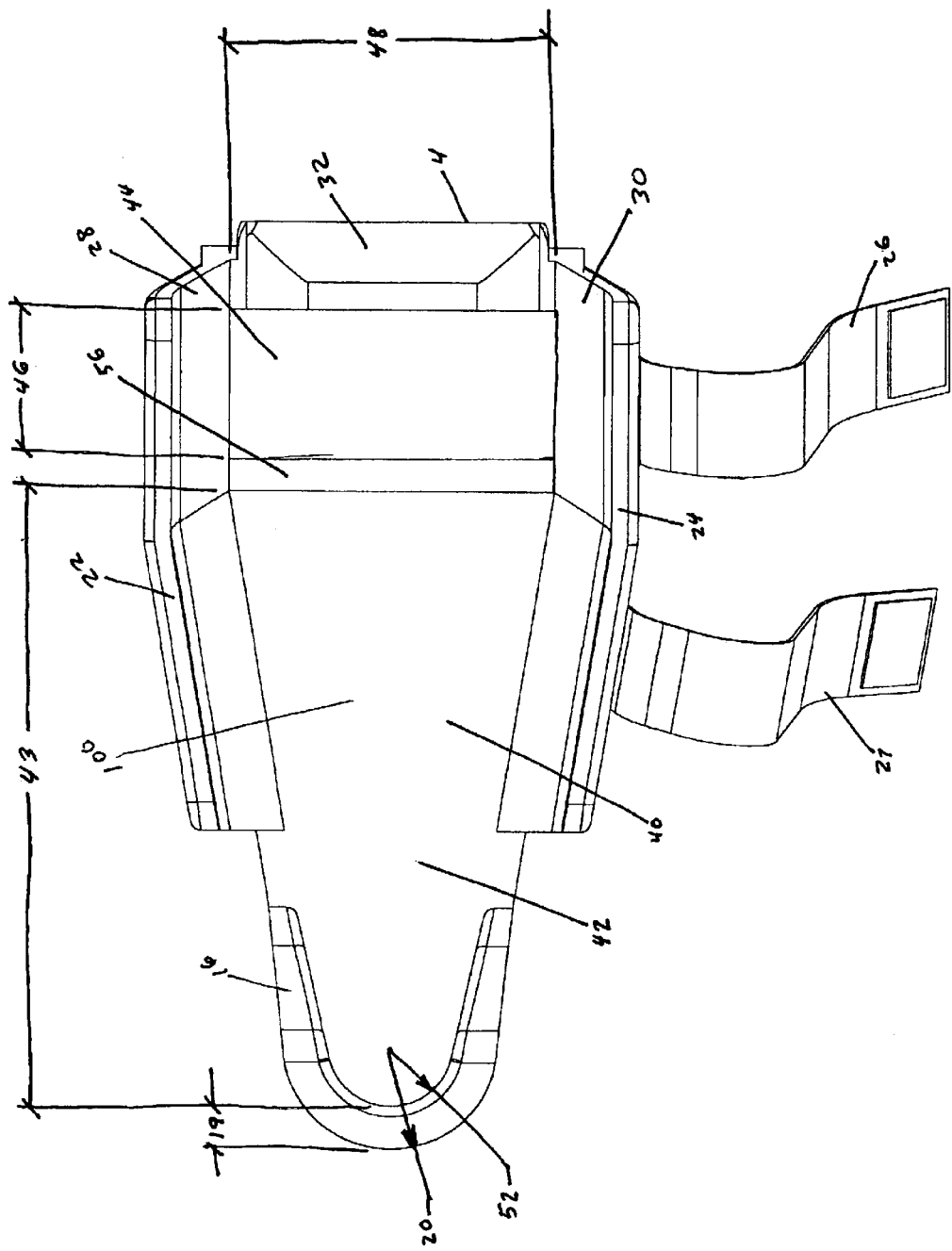
FIG. 3 is a plan view of the object of FIG. 2.
Figure 4:
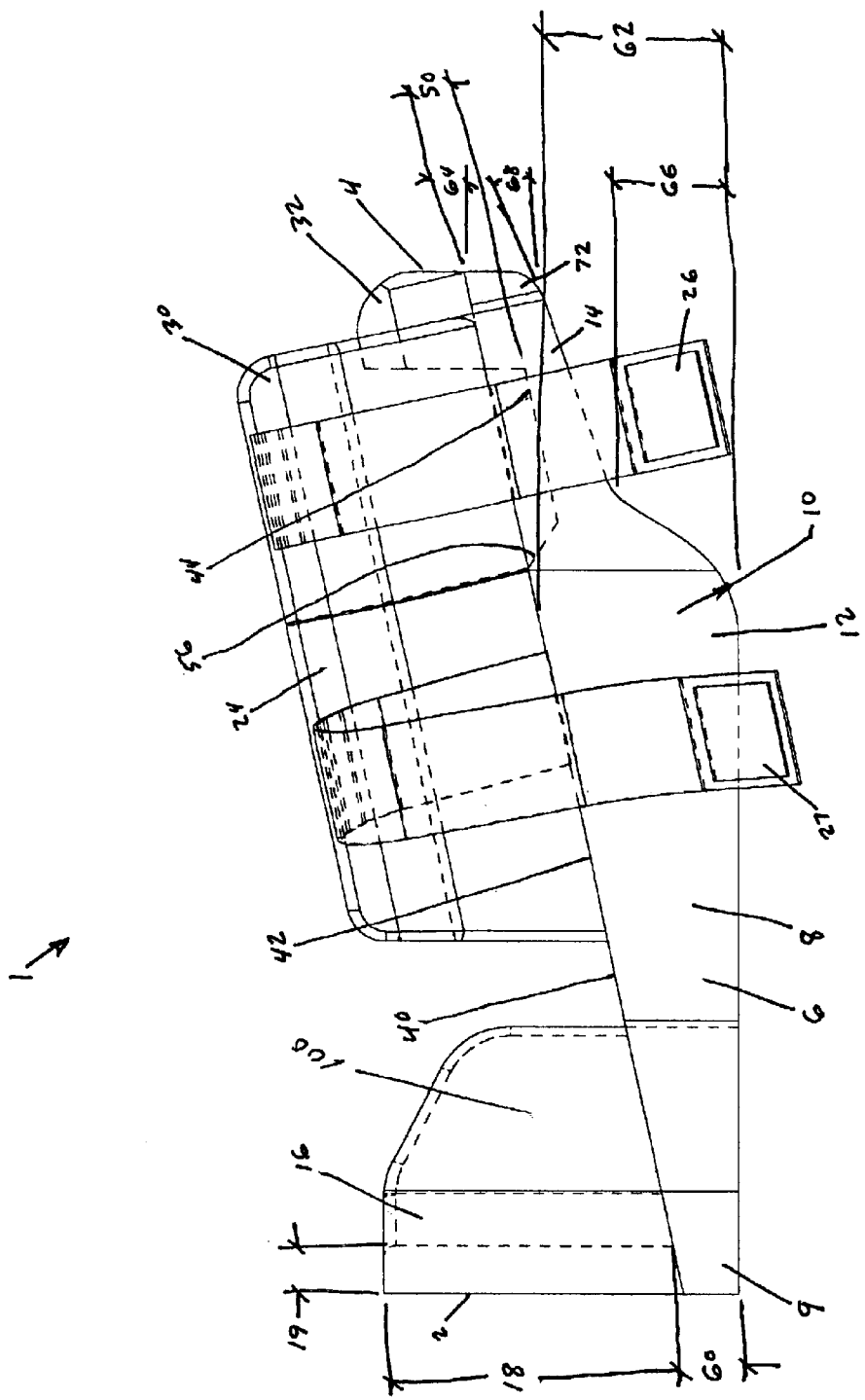
FIG. 4 is a side elevational view of the object of FIG. 2.

Referring to FIG. 1, orthosis 1 having a proximal end 2 and a distal end 4 has an outsole 6 having a proximal weight-bearing portion 8 with a proximal end 9 and a cylindrical radius 10 at its distal end 12, and a distal portion 14. At proximal end 2 of orthosis 1, more or less vertical wall 16 of height 18 and thickness 19 surrounds the proximal radius 20 so as to form a pocket which conforms closely to the heel of a user's foot. Pliant longitudinal walls 22 and 24 wrap partially over the dorsum of a user's foot and are secured with hook and loop straps 26 and 27. Distal regions 28 and 30 of longitudinal walls 22 and 24 overlap lateral distal end wall 32.

As best seen in FIGS. 2 through 5, insole 40 of orthosis 1 has a planar, proximal, weight-bearing portion 42 of length 43 extending from the heel to the distal end of the metatarsals of a user's foot, and a planar, distal portion 44 of length 46 and width 48 which is generally parallel to proximal portion 42 but recessed distance 50 below proximal portion 42. The proximal portion 42 of radius 52 at its proximal end increases to width 48 at its distal end 54 so as to generally conform to the shape of a user's foot. Regions 42 and 44 are joined by beveled surface 56.

Weight-bearing, proximal region 8 of outsole 6 of height 60 at proximal end 9 increases in thickness to height 62 at distal end 12 so as to incline insole 40 at angle 64, height 60 approximating the heel height of a sneaker or dress shoe. Distal portion 14 of outsole 6 is displaced vertically distance 66 above the distal end 12 of the proximal portion 8 and is angled upward at angle 68 so that orthosis 1 can pivot on radius 10 through an angle 70 as would occur during walking, without distal end 72 of outsole 6 contacting the floor.

Figure 5:
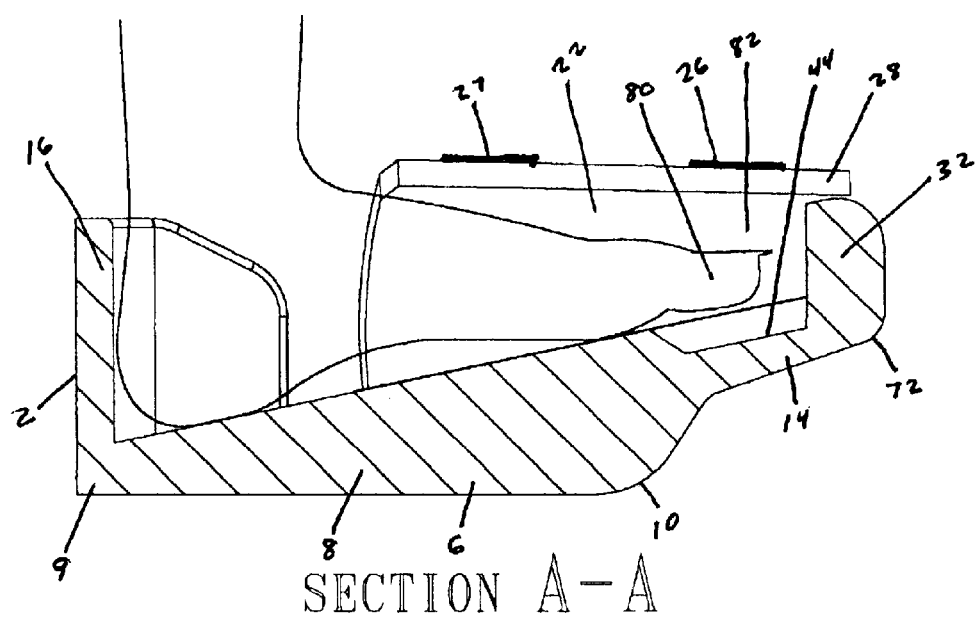
FIG. 5 is a side sectional view of an orthosis constructed in accordance with the principles of this invention with a superimposed foot profile as during use.

Referring to FIG. 5, during use a user's toes 80 are surrounded by a toe box 82 formed on the bottom by the recessed distal portion 44 of insole 40, with lateral sides and top formed by the distal portions of the wrapped longitudinal walls 22 and 24 (not shown) and on its distal end by wall 32. Toe box 82 is of sufficient size to preclude contact between toes 80 with associated dressings and the interior of orthosis 1.

Figure 6:
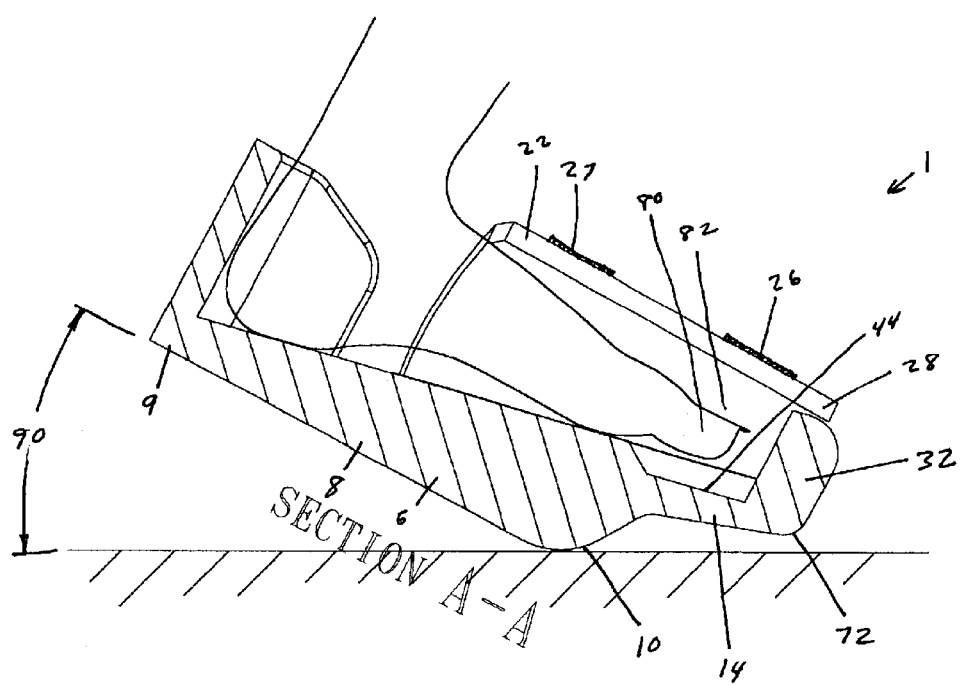
FIG. 6 is a side sectional view of an orthosis constructed in accordance with the principles of this invention with a superimposed foot profile as during use with the orthosis rotated as would occur during use for walking.

Referring to FIG. 6, during ambulation, orthosis 1 pivots through angle 90 on the fulcrum formed by radius 10 of proximal portion 8 of outsole 6 so as to give maximum launch. However, distal end 72 of distal portion 14 of outsole 6 does not contact floor 92. Since heel thickness 60 of orthosis 1 is comparable in height to that of a standard shoe, walking with a somewhat normal gait is possible if a shoe having a comparable heel thickness is worn on the uninjured foot.

Referring again to FIGS. 3 and 4, an inner volume 100 is defined by the inner surfaces of lateral walls 22 and 24, of proximal wall 16 and of lateral distal wall 32 of orthosis 1. Orthosis 1 can be molded in a mold of simple construction since the surfaces defining volume 100 allow the mold half which produces the volume to be withdrawn in a simple linear motion. Similarly, orthosis 1 can be withdrawn from the mating mold half with a simple linear motion. A slight draft angle can be imparted to vertical surfaces to aid in the molding process.

Although the invention has been taught with specific reference to the preferred embodiment, someone skilled in the art will recognize that changes can be made in form and detail without departing from the spirit and scope of the invention. The described embodiments are to be considered only as illustrative and not restrictive. The scope of the invention is, therefore, indicated by the appended claims rather than by the foregoing description.

What is claimed is:

1. An orthosis for the treatment of toe injuries comprising a monolithic structure molded form a polymeric foam material further comprising: a lower portion comprising (a) an outsole and (b) an insole, wherein said insole is formed by the upper surface of said outsole, an upper portion comprising (a) a curved vertically projecting rearward portion which conforms closely to the heel of a foot; (b) two pliable, longitudinally extending and laterally opposed side portions, each of which curve toward the other so as to wrap around the dorsum of a foot; and (c) a forward portion attached to the distal end of said insole and comprising a relatively vertical lateral wall positioned at the end of the orthosis to protect the toes from injury during ambulation.

2. The orthosis of claim 1, wherein said lateral wall is perpendicularly disposed to said insole.

3. The orthosis of claim 1, wherein said orthosis is bilaterally symmetrical.

4. The orthosis of claim 1, wherein said polymeric foam material is a closed cell polyethylene foam.

5. The orthosis of claim 1, wherein said polymeric foam material is a closed cell polypropylene foam.

6. The orthosis of claim 1, further comprising a securing mechanism to draw said longitudinal walls about the dorsum of the user's foot.

7. The orthosis of claim 6, wherein said securing mechanism comprises coordinating hook and loop straps.

8. The orthosis of claim 1, wherein said outsole comprises: (i) a proximal portion, extending from the proximal end of the orthosis and terminating in an upwardly sloping curved surface disposed under the ball of a user's foot, that increases in thickness distally so as to cause the insole to be inclined, and (ii) a distal portion, connected to said proximal portion by said curved surface, that is elevated above said proximal portion such that when said orthosis is pivoted on said curved surface during ambulation, the distal end of said outsole does not contact the floor.

9. The orthosis of claim 8, wherein the curved surface of the proximal portion of said outsole has a radius of at least 0.25 inches.

10. The orthosis of claim 8, wherein the proximal portion of said outsole is wedge-shaped.

11. The orthosis of claim 8, wherein the distal portion of said outsole slopes upwardly distally.

12. The orthosis of claim 8, wherein the angle of inclination of said insole is between five and sixteen degrees.

13. The orthosis of claim 1, wherein said insole comprises (i) a relatively planar proximal portion that extends from the proximal end of the orthosis and terminates just distal of the ball of a user's foot, and (ii) a relatively planar distal portion connected to said proximal portion by a downwardly sloping beveled surface so as to form a recess that prevents a user's toes from contacting the insole.

14. An orthosis for the treatment of toe injuries comprising a monolithic structure molded from a polymeric foam material, further comprising: a lower portion comprising (a) an outsole and (b) an insole, wherein said insole is formed by the upper surfaces of said outsole, further wherein said outsole comprises: (l) a proximal portion, extending from the proximal end of the orthosis and terminating in an upwardly sloping curved surface disposed under the ball of a user's foot, that increases in thickness distally so as to cause the insole to be inclined, and (ii) a distal portion connected to said proximal portion by said curved surface, that is elevated above said proximal portion such that when said orthosis is pivoted on said curved surface during ambulation, the distal end of said outsole does not contact the floor; and an upper portion comprising (a) a curved vertically projecting rearward portion which conforms closely to the heel of a foot; (b) two pliable, longitudinal, laterally opposed side portions each of which curves to wrap around the dorsum of a foot; and (c) a forward portion, attached to the distal end of said insole and comprising a relatively vertical lateral wall positioned at the end of the orthosis to protect the toes from injury during ambulation.

15. The orthosis of claim 14, wherein said lateral wall is attached to the distal portion of said insole and perpendicularly disposed thereto.

16. The orthosis of claim 14, wherein said orthosis is bilaterally symmetrical.

17. The orthosis of claim 14, wherein said polymeric foam material is a closed cell polypropylene foam.

18. The orthosis of claim 14, further comprising a securing mechanism to draw said longitudinal walls about the dorsum of the user's foot.

19. The orthosis of claim 18, wherein said securing mechanism comprises coordinating hook and loop straps.

20. The orthosis of claim 14, wherein the proximal portion of said outsole is wedge-shaped.

21. The orthosis of claim 14, wherein the curved surface of the proximal portion of said outsole has a radius of at least 0.25 inches.

22. The orthosis of claim 14, wherein the distal portion of said outsole slopes upwardly distally.

23. The orthosis of claim 14, wherein the angle of inclination of said insole is between five and sixteen degrees.

24. The orthosis of claim 14, wherein said insole comprises (i) a relatively planar proximal portion that extends from the proximal end of the orthosis and terminates just distal of the ball of a user's foot, and (ii) a relatively planar distal portion connected to said proximal: portion by a downwardly sloping beveled surface so as to form a recess that prevents a user's toes from contacting the insole.

25. An orthosis for the treatment of toe injuries comprising: a lower portion comprising (a) an outsole and (b) an insole, wherein said insole is formed by the upper surfaces of said outsole, further wherein said insole comprises (i) a relatively planar proximal portion that extends from the proximal end of the orthosis and terminates just distal of the ball of a user's foot; and, (ii) a relatively planar distal portion connected to said proximal portion by a downwardly sloping beveled surface so as to form a recess that prevents a user's toes from contacting the insole; and an upper portion comprising (a) a curved vertically projecting rearward portion which conforms closely to the heel of a foot; (b) two pliable, longitudinal, laterally opposed side portions each of which curves to wrap around the dorsum of a foot; and (c) a forward portion attached to the distal end of said insole and comprising a relatively' rigid vertical lateral wall positioned at the end of the orthosis to protect the toes from injury during ambulation.

26. The orthosis of claim 25, wherein said lateral wall is attached to the distal portion of said insole and perpendicularly disposed thereto.

27. The orthosis of claim 25, wherein said orthosis is bilaterally symmetrical.

28. The orthosis of claim 25, wherein said orthosis is a monolithic structure molded from a polymeric foam material.

29. The orthosis of claim 28, wherein said polymeric foam material is a closed cell polyethylene foam.

30. The orthosis of claim 28, wherein said polymeric foam material is a closed cell polypropylene foam.

31. The orthosis of claim 25, further comprising a securing mechanism to draw said longitudinal walls about the dorsum of the user's foot.

32. The orthosis of claim 31, wherein said securing mechanism comprises coordinating hook and loop straps.

33. The orthosis of claim 25, wherein said outsole comprises: (i) a proximal portion, extending foam the proximal end of the orthosis and terminating in an upwardly sloping curved surface disposed under the ball of a user's foot, that increases in thickness distally so as to cause the insole to be inclined and (ii) a distal portion connected to said proximal portion by said curved surface, that is elevated above said proximal portion such that when said orthosis is pivoted on said curved surface during ambulation, the distal end of said outsole does not contact the floor.

34. The orthosis of claim 33, wherein the proximal portion of said outsole is wedge-shaped.

35. The orthosis of claim 33, wherein the curved surface of the proximal portion of said outsole has a radius of at least 0.25 inches.

36. The orthosis of claim 33, wherein the distal portion of said outsole slopes upwardly distally.

37. The orthosis pf claim 33, wherein the angle of inclination of said insole is between five and sixteen degrees.

38. An orthosis for the treatment of toe injuries comprising a monolithic structure molded from a polymeric foam material, further comprising: a lower portion comprising (a) an outsole and (b) an insole, wherein said insole is formed by the upper surfaces of said outsole, further wherein: said outsole comprises: (i) a proximal portion, extending from the proximal end of the orthosis and terminating in an upwardly sloping curved surface disposed under the ball of a user's foot, that increases in thickness distally so as to cause the insole to be inclined, and (ii) a distal portion connected to said proximal portion by said curved surface that is elevated above said proximal portion such that when said orthosis is pivoted on said curved surface during ambulation, the distal end of said outsole does not contact the floor, and said insole comprises (i) a relatively planar proximal portion that extends from the proximal end of the orthosis and terminates just distal of the ball of a user's foot, and (ii) a relatively planar distal portion connected to said proximal potion by a downwardly sloping beveled surface so as to form a recess that prevents a user's toes from contacting the insole', and an upper portion comprising (a) a curved vertically projecting rearward portion which conforms closely to the heel of a foot; (b) two pliable, longitudinal, laterally opposed side portions, each of which curves to wrap around the dorsum of a foot; and (c) a forward portion attached to the distal end of said insole and comprising a relatively vertical lateral wall positioned at the end of the orthosis to protect the toes from injury during ambulation.

39. The orthosis of caim 38, wherein said lateral wall is attached to the distal portion of said insole and perpendicularly disposed thereto.

40. The orthosis of claim 38, wherein said orthosis is bilaterally symmetrical.

41. The orthosis of claim 38, wherein said polymeric foam material is a dosed cell polyethylene foam.

42. The orthosis of claim 38, wherein said polymeric foam material is a closed cell polypropylene foam.

43. The orthosis of claim 38, further comprising a securing mechanism to draw said longitudinal walls about the dorsum at the user's foot.

44. The orthosis of claim 43, wherein said securing mechanism comprises coordinating hook and loop straps.

45. The orthosis of claim 38, wherein the proximal portion of said outsole is wedge-shaped.

46. The orthosis of claim 38, wherein the curved surface of the proximal portion of said outsole has a radius of at least 0.25 inches.

47. The orthosis of claim 38, wherein the distal portion of said outsole slopes upwardly distally.

48. The orthosis of claim 38, wherein the angle of inclination of said insole is between five and sixteen degrees.

* * * * *

UNITED STATES PATENT AND TRADEMARK OFFICE
CERTIFICATE OF CORRECTION

PATENT NO. : 7,004,918 B2
APPLICATION NO. : 10/442195
DATED : February 28, 2006
INVENTOR(S) : Rolnick et al.

It is certified that error appears in the above-identified patent and that said Letters Patent is hereby corrected as shown below:

On the Title page, Item (76) "Inventors", please change Inventor name "Matthew Ferry Warden" to -- Matthew Perry Warden--.

column 5, line 19, please change "form" to -- from --.

Signed and Sealed this

Fifteenth Day of August, 2006

JON W. DUDAS
*Director of the United States Patent and Trademark Office*